United States Patent [19]

Sasaki et al.

[11] Patent Number: 4,880,936
[45] Date of Patent: Nov. 14, 1989

[54] OPTICALLY ACTIVE PYRIDINES USEFUL IN LIQUID CRYSTAL FORM FOR ELECTRICAL DISPLAY DEVICES

[75] Inventors: Makoto Sasaki, Saitama; Kiyohumi Takeuchi; Haruyoshi Takatsu, both of Tokyo, all of Japan

[73] Assignee: Dainippon Ink and Chemicals, Inc., Tokyo, Japan

[21] Appl. No.: 172,923

[22] Filed: Mar. 25, 1988

[30] Foreign Application Priority Data

Mar. 26, 1987 [JP] Japan .................................. 62-70174

[51] Int. Cl.$^4$ ............................................. C07D 213/30
[52] U.S. Cl. .............................. 546/339; 350/350 R; 350/350 S; 546/346
[58] Field of Search ........................................ 546/339

[56] References Cited

FOREIGN PATENT DOCUMENTS

| | | | |
|---|---|---|---|
| 0160416A2 | 11/1985 | European Pat. Off. | 544/238 |
| 0228303A1 | 7/1987 | European Pat. Off. | |
| 0288303A1 | 7/1987 | European Pat. Off. | 546/339 |
| 0233706A2 | 8/1987 | European Pat. Off. | 546/339 |
| 0260910A1 | 3/1988 | European Pat. Off. | 544/238 |
| 61-215373 | 9/1986 | Japan | 544/335 |
| 2153345A | 8/1985 | United Kingdom | 546/330 |
| WO86/06373 | 11/1986 | World Int. Prop. O. | 544/408 |

Primary Examiner—Alan L. Rotman
Attorney, Agent, or Firm—Armstrong, Nikaido, Marmelstein, Kubovcik & Murray

[57] ABSTRACT

An optically active compound represented by formula (I):

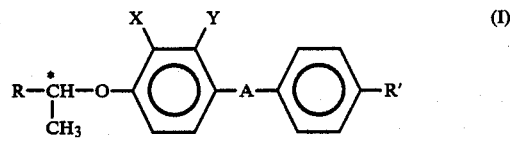

wherein R represents a straight chain alkyl group having from 2 to 12 carbon atoms; R' represents a straight chain alkyl or alkoxy group having from 1 to 20 carbon atoms; C represents an asymmetric carbon atom; A represents

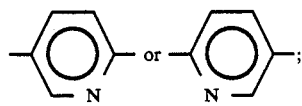

and X and Y each represents a hydrogen atom or a fluorine atom, provided that X and Y do not simultaneously represent a fluorine atom. The compound (I) reduces a temperature dependence of the threshold voltage of a nematic liquid crystal composition when added thereto in a small amount.

19 Claims, 1 Drawing Sheet

OPTICALLY ACTIVE PYRIDINES USEFUL IN LIQUID CRYSTAL FORM FOR ELECTRICAL DISPLAY DEVICES

FIELD OF THE INVENTION

This invention relates to optically active pyridines which are useful as an electro-optical display material.

BACKGROUND OF THE INVENTION

In recent years, liquid crystal display cells of high multiplexing driving systems have been gradually increased in size, leading to an increasing demand as displays for computer terminals, TV sets and so forth. With this increase in demand, liquid crystal materials having high level multiplexibility have been more needed.

High level multiplexing driving systems are depending on change in environmental temperature and a cross-talk phenomenon will easily occur. In order to prevent the formation of the cross-talk phenomenon due to changes in the environmental temperature, the following have been known; (1) a method in which a temperature compensation circuit is provided in the liquid crystal display equipment; and (2) a method in which the temperature dependency of threshold voltage of liquid crystal material is decreased by adding a chiral substance the molecular orientation of which is twisted right and a chiral substance the molecular orientation of which is twisted left, to the liquid crystal material. The method (1), however, has a disadvantage in that the equipment becomes expensive. Also the method (2) has a disadvantage in that the amount of the substances added is limited because if the amount of the substances added is increased, the response time is decreased, although the substances are necessary to add in large amounts in order to sufficiently obtain the desired effect; therefore the desired effect cannot be obtained sufficiently.

SUMMARY OF THE INVENTION

An object of this invention is to efficiently prevent the cross-talk phenomenon due to changes in environmental temperature in high level multiplexing driving systems.

Another object of this invention is to provide novel pyridine derivatives which when added to various practical nematic liquid crystal compositions, are able to sufficiently decrease the temperature dependency of threshold voltage of the compositions even in small amounts.

It has been found that the objects can be attained by using compounds represented by the general formula (I) as described hereinafter.

This invention provides optically active pyridines represented by the general formula (I):

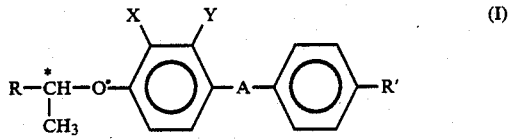

(wherein R represents a straight chain alkyl group having from 2 to 12 carbon atoms; R' represents a straight chain alkyl or alkoxy group having from 1 to 20 carbon atoms; * represents an asymmetric carbon atom; A represents

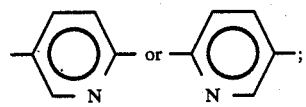

and X and Y each represents a hydrogen atom or a fluorine atom, provided that X and Y do not simultaneously represent a fluorine atom).

BRIEF DESCRIPTION OF THE ACCOMPANYING DRAWING

FIG. 1 shows a temperature dependence of the threshold voltage for each of the host liquid crystal (A) and a mixed liquid crystal comprising said host liquid crystal (A) and 0.84% by weight of the optically active compound No. 1 of the present invention.

DETAILED DESCRIPTION OF THE INVENTION

Figure 1:
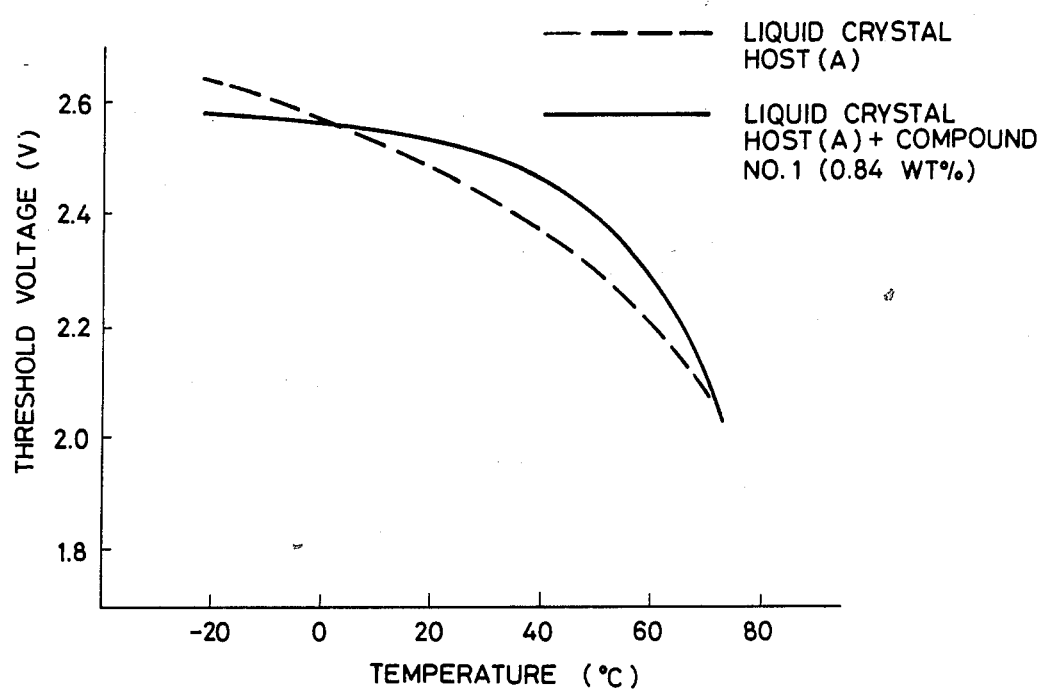

The compound represented by formula (I) can be prepared by reacting a compound represented by formula (II):

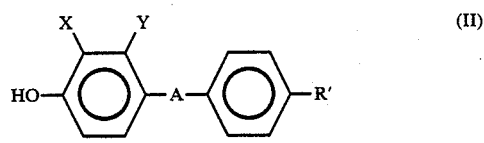

wherein R', A, X and Y are defined above, with an optically active tosylate represented by formula (III):

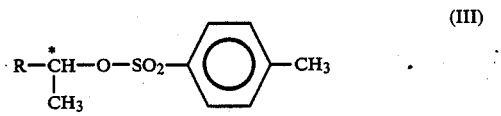

wherein R and * are as defined above, in a solvent, such as dimethyl sulfoxide, in the presence of a base, such as potassium t-butoxide.

Typical compounds represented by formula (I) are shown in Table 1 below together with their transition temperatures and optical rotations. In Table 1, C means a crystal phase; Sc* means a chiral smectic phase; $S_A$ means a smectic A phase; N* means a chiral nematic phase; I means an isotropic liquid phase; $S_4$ means a high-order smectic phase; and $S_B$ means a smectic B phase.

TABLE 1

$$R-\overset{*}{C}H-O-\underset{}{\text{(ring with X,Y)}}-A-\text{(ring)}-R'$$
with CH₃ on the chiral carbon, X and Y substituents on the first ring.

| Compound No. | R | R' | —A— | X | Y | Transition Temperature (°C.) | Optical Rotation $[\alpha]_D^{25}$ |
|---|---|---|---|---|---|---|---|
| 1 | n-C$_6$H$_{13}$— | n-C$_5$H$_{11}$— | pyridine-2,5-diyl | H | H | 58 (C → Sc*)<br>115 (Sc* ⇌ S$_A$)<br>116 (S$_A$ ⇌ N*)<br>117 (N* ⇌ I) | +3.50 |
| 2 | n-C$_6$H$_{13}$— | n-C$_5$H$_{11}$— | pyridine-2,5-diyl | H | H | 78 (C → S$_A$)<br>139 (S$_A$ ⇌ I) | +2.90 |
| 3 | n-C$_{10}$H$_{21}$— | n-C$_5$H$_{11}$— | pyridine-2,5-diyl | H | H | 70 (C → S$_A$)<br>127 (S$_A$ ⇌ I) | +11.10 |
| 4 | n-C$_6$H$_{13}$— | n-C$_5$H$_{11}$O— | pyridine-2,5-diyl | H | H | 104 (C → S$_4$)<br>117 (S$_4$ ⇌ S$_B$)<br>132 (S$_B$ ⇌ Sc*)<br>142 (Sc* ⇌ S$_A$)<br>165 (S$_A$ ⇌ I) | +5.80 |
| 5 | n-C$_6$H$_{13}$— | n-C$_5$H$_{11}$— | pyridine-2,5-diyl | F | H | 84 (C → S$_A$)<br>124 (S$_A$ ⇌ I) | +3.10 |
| 6 | n-C$_6$H$_{13}$— | n-C$_5$H$_{11}$— | pyridine-2,5-diyl | H | F | 31 (C → N*)<br>56 (N* ⇌ I) | +3.00 |

By adding a small amount of the compound of formula (I) to a number of nematic liquid crystal compositions commonly employed at present, temperature dependence of the threshold voltage of the liquid crystal compositions can be reduced sufficiently.

FIG. 1 shows the temperature dependence of the threshold voltage for each of a host liquid crystal (A) having the following composition which is of present use as nematic liquid crystal material and a nematic liquid crystal composition comprising the host liquid crystal (A) having incorporated thereto 0.84% by weight of Compound 1 according to the present invention. This nemtaic liquid crystal composition has a pitch of 100 μm.

Composition of Host Liquid Crystal (A):

| Structure | Ratio (wt %) |
|---|---|
| 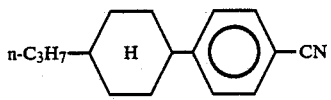 n-C₃H₇—H—⬡—CN | 13 |
| 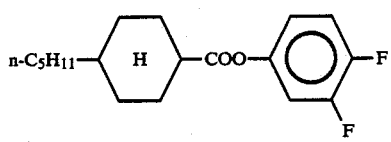 n-C₅H₁₁—H—COO—⬡(3,4-F₂) | 9 |
| 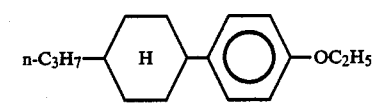 n-C₃H₇—H—⬡—OC₂H₅ | 13 |
| 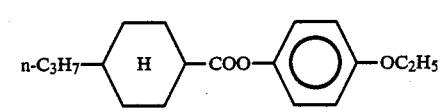 n-C₃H₇—H—COO—⬡—OC₂H₅ | 10 |
| 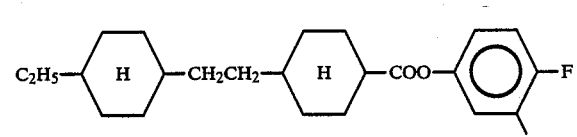 C₂H₅—H—CH₂CH₂—H—COO—⬡(3,4-F₂) | 2 |
| 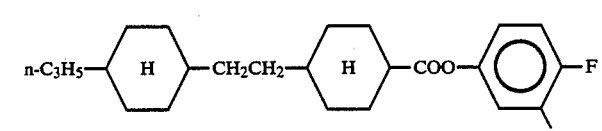 n-C₃H₇—H—CH₂CH₂—H—COO—⬡(3,4-F₂) | 7 |
| 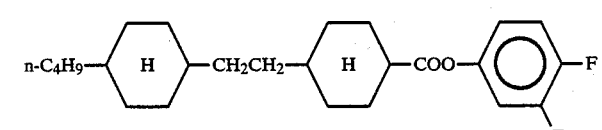 n-C₄H₉—H—CH₂CH₂—H—COO—⬡(3,4-F₂) | 5 |
| 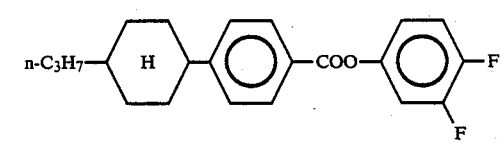 n-C₃H₇—H—⬡—COO—⬡(3,4-F₂) | 5 |
| 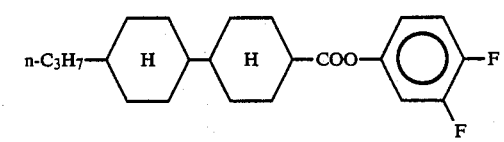 n-C₃H₇—H—H—COO—⬡(3,4-F₂) | 5 |
| 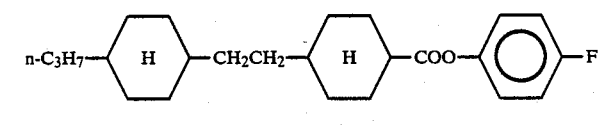 n-C₃H₇—H—CH₂CH₂—H—COO—⬡—F | 9 |
|  C₂H₅—H—COO—⬡—CH₂CH₂—H—n-C₃H₇ | 4 |

-continued

| | Ratio (wt %) |
|---|---|
| 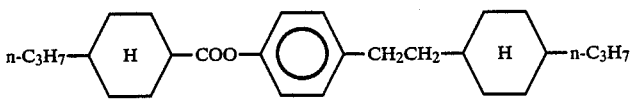 n-C3H7—⟨H⟩—COO—⟨◯⟩—CH2CH2—⟨H⟩—n-C3H7 | 4 |
| 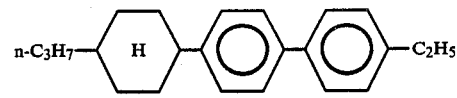 n-C3H7—⟨H⟩—⟨◯⟩—⟨◯⟩—C2H5 | 8 |
| 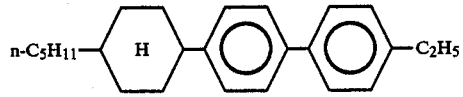 n-C5H11—⟨H⟩—⟨◯⟩—⟨◯⟩—C2H5 | 7 |

Table 2 below shows a pitch and a difference between the threshold voltage at 0° C. and that at 40° C. for various mixed liquid crystal compositions prepared by mixing the host liquid crystal (A) and each of Compounds 1 to 6 according to this invention.

TABLE 2

| Mixed Liquid Crystal | Amount of Compound (I) Added (wt %) | Pitch (μm) | Difference in Threshold Voltage (mV) |
|---|---|---|---|
| (A) | — | | 208 |
| (A) + Compound 1 | 0.840 | 100 | 108 |
| (A) + Compound 2 | 0.654 | 100 | 112 |
| (A) + Compound 3 | 0.681 | 100 | 111 |
| (A) + Compound 4 | 0.842 | 100 | 94 |
| (A) + Compound 5 | 0.410 | 100 | 103 |
| (A) + Compound 6 | 0.518 | 100 | 107 |

It can be seen from Table 2 that addition of a small amount of the compound according to this invention to a nematic liquid crystal composition produces a sufficient effect to reduce temperature dependence of the threshold voltage of the composition.

The compounds of formula (I) are also applicable as liquid crystal material for ferroelectric liquid crystal display elements proposed by Clerk, et al. in *Appl. Phys. Lett.*, Vol. 36, 899 (1980). Among the compounds of formula (I), Compound 1 is of particular advantage because it has a broad chiral smectic C phase and the series of phase transition is suited for orientation.

The optically active compounds in accordance with this present invention reduce a temperature dependence of the threshold voltage of a nematic liquid crystal composition when added thereto in a small amount. Therefore, the compounds can be effectively used in the preparation of liquid crystal materials which can be prevented effectively from suffering a cross-talk phenomenon due to change of environmental temperature in a high level multiplexing driving system.

The present invention is now illustrated in greater detail with reference to the following examples, but it should be understood that the present invention is not deemed to be limited thereto.

EXAMPLE 1

In 30 ml of dimethyl sufixide was dissolved 3.2 g (0.010 mol) of a compound of formula:

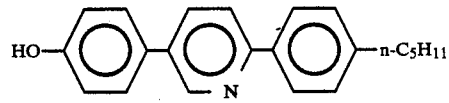

HO—⟨◯⟩—⟨◯N⟩—⟨◯⟩—n-C5H11 and 1.5 g (0.013 mol) of potassium t-butoxide was added to the solution. After stirring the mixture at room temperature for 30 minutes, 2.9 g (0.010 mol) of (S) (+)-2-octyl tosylate was added thereto, followed by allowing the mixture to react at 50° C. for 5 hours. After completion of the reaction, the reaction mixture was poured into 100 ml of ice-water, followed by extraction with toluene. The extract was washed with water and dried. The solvent was removed by distillation under reduced pressure, and the residue was purified by recrystallization from ethanol to obtain 32. g (0.0075 mol) of compound represented by

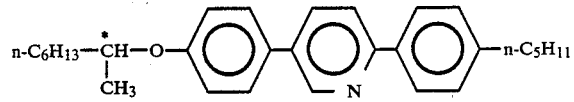

n-C6H13—*CH—O—⟨◯⟩—⟨◯N⟩—⟨◯⟩—n-C5H11
          |
          CH3 in a yield of 75%.

In the same manner as described above, compounds shown in Table 3 below were prepared.

TABLE 3

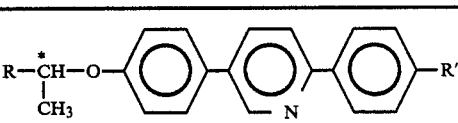

R—*CH—O—⟨◯⟩—⟨◯N⟩—⟨◯⟩—R'
    |
    CH3

| R | R' |
|---|---|
| C2H5— | —N—C3H7 |
| n-C3H7— | —O—n-C7H15 |
| n-C4H9— | —n-C12H25 |
| n-C5H11— | —O—n-C17H35 |
| n-C6H13— | —C2H5 |
| n-C6H13— | —O—C2H5 |
| n-C6H13— | —O—n-C5H11 |
| n-C6H13— | —n-C8H17 |
| n-C6H13— | —O—n-C8H17 |
| n-C6H13— | —n-C10H21 |
| n-C6H13— | —O—n-C10H21 |
| n-C6H13— | —n-C13H27 |
| n-C6H13— | —O—n-C13H27 |
| n-C6H13— | —n-C19H39 |
| n-C6H13— | —O—n-C19H39 |
| n-C7H15— | —n-C4H9 |

TABLE 3-continued

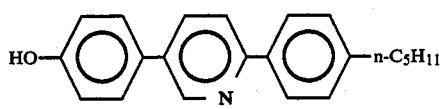

| R | R' |
|---|---|
| n-C$_8$H$_{17}$— | —O—n-C$_6$H$_{13}$ |
| n-C$_9$H$_{19}$— | —n-C$_{15}$H$_{31}$ |
| n-C$_{10}$H$_{21}$— | —O—n-C$_5$H$_{11}$ |
| n-C$_{11}$H$_{23}$— | —n-C$_{14}$H$_{29}$ |
| n-C$_{12}$H$_{25}$— | —O—n-C$_{18}$H$_{37}$ |

EXAMPLE 2

In the same manner as in Example 1, except for replacing the compound of formula:

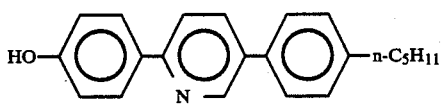

with a compound of formula

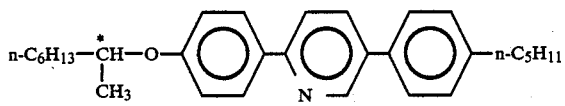

to obtain a compound of

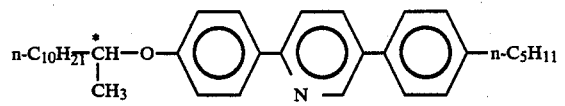

in a yield of 67%.

EXAMPLE 3

A compound of

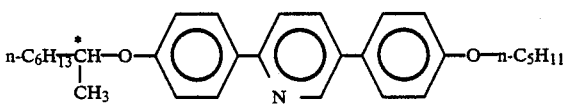

was prepared in the same manner as in Example 2, in a yield of 56%.

EXAMPLE 4

A compound of n-C$_6$H$_{13}$—*CH—O—[ring]—[ring-N]—[ring]—O—n-C$_5$H$_{11}$ (with CH$_3$)

was prepared in the same manner as in Example 2. Yield: 58%.

Table 4 below shows compounds which can be prepared in the same manner as in Example 2.

TABLE 4

R—*CH—O—[ring]—[ring-N]—[ring]—R' (with CH$_3$)

| R | R' |
|---|---|
| C$_2$H$_5$— | —C$_2$H$_5$ |
| n-C$_3$H$_7$— | —O—n-C$_6$H$_{13}$ |
| n-C$_4$H$_9$— | —n-C$_{11}$H$_{23}$ |
| n-C$_5$H$_{11}$— | —O—n-C$_{16}$H$_{33}$ |
| n-C$_6$H$_{13}$— | —n-C$_3$H$_7$ |
| n-C$_6$H$_{13}$— | —O—n-C$_3$H$_7$ |
| n-C$_6$H$_{13}$— | —n-C$_6$H$_{13}$ |
| n-C$_6$H$_{13}$— | —O—n-C$_6$H$_{13}$ |
| n-C$_6$H$_{13}$— | —n-C$_8$H$_{17}$ |
| n-C$_6$H$_{13}$— | —O—n-C$_8$H$_{17}$ |
| n-C$_6$H$_{13}$— | —n-C$_{10}$H$_{21}$ |
| n-C$_6$H$_{13}$— | —O—n-C$_{10}$H$_{21}$ |
| n-C$_6$H$_{13}$— | —n-C$_{12}$H$_{25}$ |
| n-C$_6$H$_{13}$— | —O—n-C$_{12}$H$_{25}$ |
| n-C$_7$H$_{15}$— | —n-C$_3$H$_7$ |
| n-C$_8$H$_{17}$— | —O—n-C$_8$H$_{17}$ |
| n-C$_9$H$_{19}$— | —n-C$_{14}$H$_{29}$ |
| n-C$_{11}$H$_{23}$— | —O—n-C$_{10}$H$_{21}$ |
| n-C$_{12}$H$_{25}$— | —n-C$_{20}$H$_{41}$ |

EXAMPLE 5

In the same manner as in Example 1, except for replacing the compound of formula:

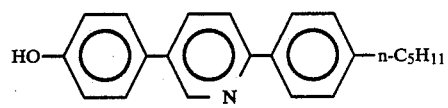

with a compound of formula:

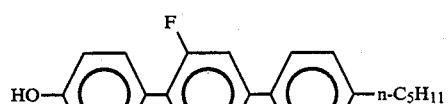

to obtain a compound of

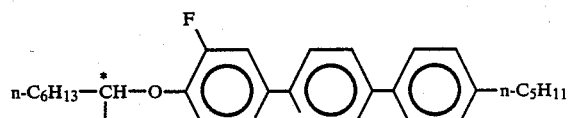

in a yield of 71%.

EXAMPLE 6

In the same manner as in Example 1, except for replacing the compound of formula:

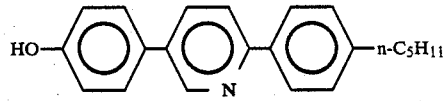

with a compound of formula:

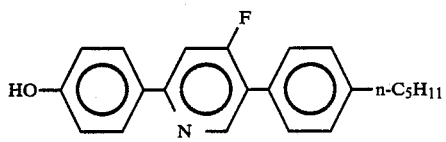

to obtain a compound of

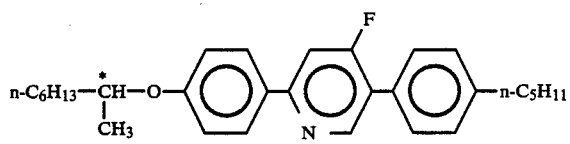

in a yield of 68%.

Table 5 below shows compounds which can be prepared in the same manner as in Example 5 or 6.

TABLE 5

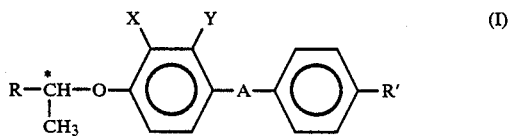

| R | X | Y | R' |
|---|---|---|---|
| $C_2H_5-$ | H | F | $-n-C_4H_9$ |
| $n-C_3H_7-$ | H | F | $-O-n-C_8H_{17}$ |
| $n-C_4H_9-$ | F | H | $-n-C_{14}H_{29}$ |
| $n-C_5H_{11}-$ | F | H | $-O-n-C_{18}H_{37}$ |
| $n-C_6H_{13}-$ | H | F | $-C_2H_5$ |
| $n-C_6H_{13}-$ | H | F | $-O-C_2H_5$ |
| $n-C_6H_{13}-$ | F | H | $-O-n-C_5H_{11}$ |
| $n-C_6H_{13}-$ | H | F | $-O-n-C_5H_{11}$ |
| $n-C_6H_{13}-$ | H | F | $-n-C_7H_{15}$ |
| $n-C_6H_{13}-$ | H | F | $-O-n-C_7H_{15}$ |
| $n-C_6H_{13}-$ | F | H | $-n-C_8H_{17}$ |
| $n-C_6H_{13}-$ | F | H | $-O-n-C_8H_{17}$ |
| $n-C_6H_{13}-$ | H | F | $-n-C_{10}H_{21}$ |
| $n-C_6H_{13}-$ | H | F | $-O-n-C_{10}H_{21}$ |
| $n-C_6H_{13}-$ | F | H | $-O-C_{11}H_{25}$ |
| $n-C_6H_{13}-$ | F | H | $-O-n-C_{12}H_{25}$ |
| $n-C_7H_{15}-$ | H | F | $-n-C_4H_9$ |
| $n-C_8H_{17}-$ | H | F | $-O-n-C_{10}H_{21}$ |
| $n-C_9H_{19}-$ | F | H | $-n-C_{11}H_{23}$ |
| $n-C_{10}H_{21}-$ | F | H | $-O-n-C_6H_{13}$ |
| $n-C_{11}H_{23}-$ | H | F | $-n-C_{11}H_{23}$ |
| $n-C_{12}H_{25}-$ | H | F | $-O-n-C_{16}H_{33}$ |

While the invention has been described in detail and with reference to specific embodiments thereof, it will be apparent to one skilled in the art that various changes and modifications can be made therein without departing from the spirit and scope thereof.

What is claimed is:

1. An optically active compound represented by formula (I):

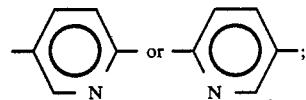

wherein R represents a straight chain alkyl group having from 2 to 12 carbon atoms; R' represents a straight chain alkyl or alkoxy group having from 1 to 20 carbon atoms; * represents an asymmetric carbon atom; A represents and X and Y each represents a hydrogen atom or a fluorine atom, provided that X and Y do not simultaneously represent a fluorine atom.

2. The compound of claim 1 represented by formula:

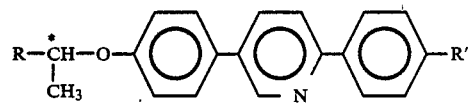

wherein R represents a straight chain alkyl group having from 2 to 12 carbon atoms; and R' represents a straight chain alkyl group having from 1 to 20 carbon atoms.

3. The compound of claim 1 represented by formula:

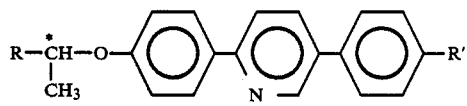

wherein R represents a straight chain alkyl group having from 2 to 12 carbon atoms; and R' represents a straight chain alkyl group having from 1 to 20 carbon atoms.

4. The compound of claim 1 represented by formula:

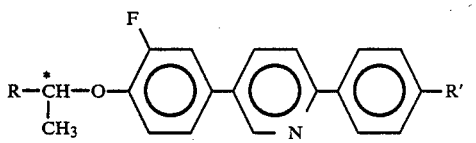

wherein R represents a straight chain alkyl group having from 2 to 12 carbon atoms; and R' represents a straight chain alkyl group having from 1 to 20 carbon atoms.

5. The compound of claim 1 represented by formula:

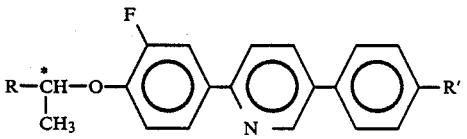

wherein R represents a straight chain alkyl group having from 2 to 12 carbon atoms; and R' represents a straight chain alkyl group having from 1 to 20 carbon atoms.

6. The compound of claim 1 represented by formula:

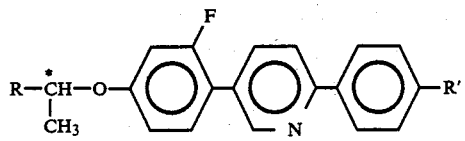

wherein R represents a straight chain alkyl group having from 2 to 12 carbon atoms; and R' represents a straight chain alkyl group having from 1 to 20 carbon atoms.

7. The compound of claim 1 represented by formula:

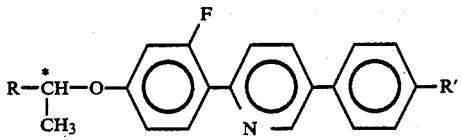

wherein R represents a straight chain alkyl group having from 2 to 12 carbon atoms; and R' represents a straight chain alkyl group having from 1 to 20 carbon atoms.

8. The compound of claim 1 represented by formula:

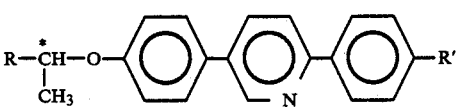

wherein R represents a straight chain alkyl group having from 2 to 12 carbon atoms; and R' represents a straight chain alkoxy group having from 1 to 20 carbon atoms.

9. The compound of claim 1 represented by formula:

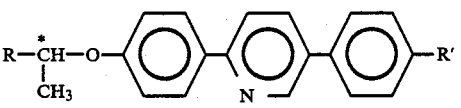

wherein R represents a straight chain alkyl group having from 2 to 12 carbon atoms; and R' represents a straight chain alkoxy group having from 1 to 20 carbon atoms.

10. The compound of claim 1 represented by formula:

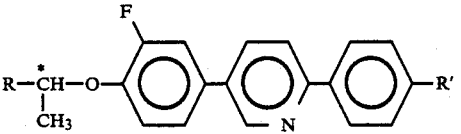

wherein R represents a straight chain alkyl group having from 2 to 12 carbon atoms; and R' represents a straight chain alkoxy group having from 1 to 20 carbon atoms.

11. The compound of claim 1 represented by formula:

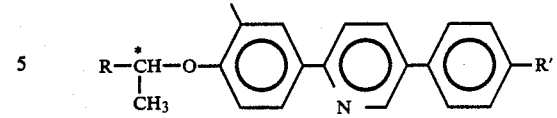

wherein R represents a straight chain alkyl group having from 2 to 12 carbon atoms; and R' represents a straight chain alkoxy group having from 1 to 20 carbon atoms.

12. The compound of claim 1 represented by formula:

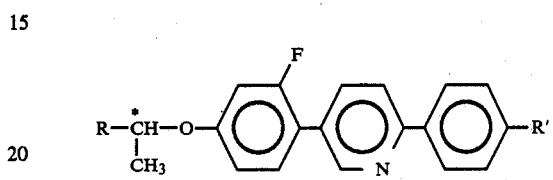

wherein R represents a straight chain alkyl group having from 2 to 12 carbon atoms; and R' represents a straight chain alkoxy group having from 1 to 20 carbon atoms.

13. The compound of claim 1 represented by formula:

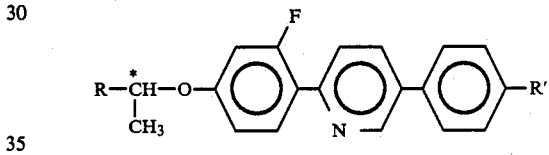

wherein R represents a straight chain alkyl group having from 2 to 12 carbon atoms; and R' represents a straight chain alkoxy group having from 1 to 20 carbon atoms.

14. The compound of claim 1 represented by formula:

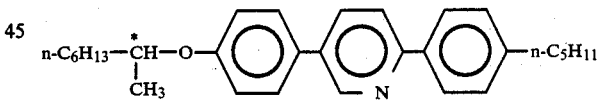

15. The compound of claim 1 represented by formula:

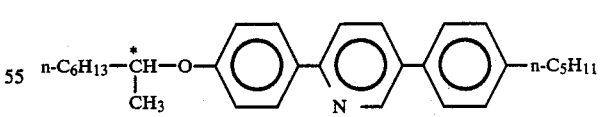

16. The compound of claim 1 represented by formula:

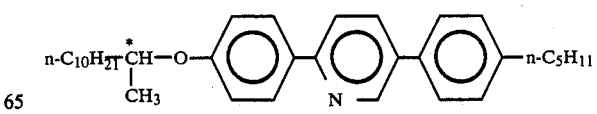

17. The compound of claim 1 represented by formula:

18. The compound of claim 1 represented by formula:
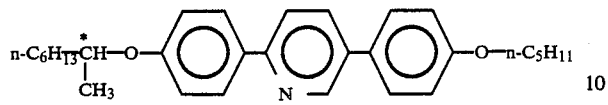
19. The compound of claim 1 represented by formula:
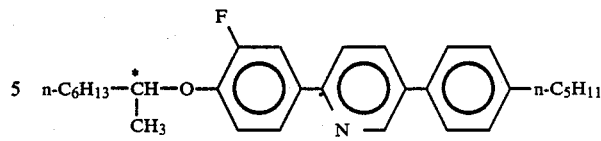
* * * * *